(12) United States Patent
Ganchi et al.

(10) Patent No.: US 11,517,251 B2
(45) Date of Patent: Dec. 6, 2022

(54) BREAST-MEASURING DEVICE

(71) Applicants: Parham A. Ganchi, Wayne, NJ (US); Reza Mollaaghababa, Natick, MA (US)

(72) Inventors: Parham A. Ganchi, Wayne, NJ (US); Reza Mollaaghababa, Natick, MA (US)

( * ) Notice: Subject to any disclaimer, the term of this patent is extended or adjusted under 35 U.S.C. 154(b) by 411 days.

(21) Appl. No.: 16/793,482

(22) Filed: Feb. 18, 2020

(65) Prior Publication Data

US 2020/0323481 A1 Oct. 15, 2020

Related U.S. Application Data

(60) Provisional application No. 62/808,103, filed on Feb. 20, 2019.

(51) Int. Cl.
*A61B 5/00* (2006.01)

(52) U.S. Cl.
CPC .......... *A61B 5/4312* (2013.01); *A61B 5/0022* (2013.01); *A61B 5/6823* (2013.01); *A61B 2562/0247* (2013.01); *A61B 2562/168* (2013.01)

(58) Field of Classification Search
CPC ............................ A61B 5/4312; A61B 5/6823
USPC ............................................. 450/81; 600/587
See application file for complete search history.

(56) References Cited

U.S. PATENT DOCUMENTS

| | | | |
|---|---|---|---|
| 4,024,856 A | 5/1977 | Kirianoff | |
| 4,219,029 A | 8/1980 | Grossman et al. | |
| 4,338,953 A | 7/1982 | Ward | |
| 2016/0089110 A1* | 3/2016 | Milkowski | A61B 8/4281 600/472 |

FOREIGN PATENT DOCUMENTS

| | | | | |
|---|---|---|---|---|
| CN | 203400148 U | | 1/2014 | |
| CN | 208371794 U | * | 1/2019 | ............ A61B 5/107 |
| KR | 200406517 Y1 | * | 11/2005 | ............... A61B 5/00 |
| RU | 76209 U1 | * | 2/2008 | ............ A61B 5/103 |
| WO | WO-2019135546 A1 | * | 12/2018 | ........... A61B 5/0055 |

OTHER PUBLICATIONS

RU-76209-U1 English translation (Year: 2008).*
KR-200406517-Y1 English translation (Year: 2005).*
CN-208371794-U English translation (Year: 2019).*
WO-2019135546-A1 English translation (Year: 2018).*
International Search Report and Written Opinion for Application No. PCT/US2020/018617, dated May 5, 2020 (11 pages).

* cited by examiner

*Primary Examiner* — Daniel L Cerioni
*Assistant Examiner* — Raymond P Dulman
(74) *Attorney, Agent, or Firm* — Barnes & Thornburg LLP

(57) ABSTRACT

In one aspect, a device for measuring breast volume is disclosed, which comprises a housing comprising an enclosure having an opening, a flexible membrane sealingly covering said opening so as to provide an enclosed space within said enclosure, a gas disposed within said enclosed space, and at least one pressure sensor coupled to said enclosure so as to measure pressure of said gas within said enclosed space. The flexible membrane is configured to reversibly flex into said enclosed space in response to pressure of a breast against the membrane. The flexure of the membrane causes a change in the pressure and volume of the gas within said enclosed space.

15 Claims, 13 Drawing Sheets

BREAST-MEASURING DEVICE

CROSS-REFERENCE TO RELATED APPLICATIONS

This application claims the benefit of U.S. Provisional Application 62/808,103, filed Feb. 20, 2019. The entire contents of this application are incorporated by reference herein.

FIELD

The present invention relates generally to devices for measuring the volume and/or asymmetry of a breast.

BACKGROUND

Surgical procedures of the breasts are some of the most common procedures performed in the United States. Over 300,000 cosmetic breast augmentation procedures and more than 100,000 breast lift procedures are performed by cosmetic plastic surgeons annually. Reconstructive surgeons perform over 100,000 breast reconstruction procedures for cancer patients and a similar number of breast reduction procedures.

For all of these procedures, the size and symmetry of the breasts are very important to a successful outcome. Currently, there is, however, no accurate method or device to determine breast size or symmetry before, during, or after surgery. In operating rooms, surgeons can only rely on rough visual estimates of breast size and symmetry. During the consultation prior to surgery, patient education and planning by the surgeon is limited to estimates and educated guesses of breast size and symmetry. After surgery, evaluation of the success of the surgery is also limited to subjective appraisals.

Accordingly, there is a need for devices and methods for measuring breast size and/or symmetry both in and outside an operating room.

SUMMARY

In one aspect, a device for measuring breast volume is disclosed, which comprises a housing comprising an enclosure having an opening, a flexible membrane sealingly covering said opening so as to provide an enclosed space within said enclosure, a gas disposed within said enclosed space, and at least one pressure sensor coupled to said enclosure so as to measure pressure of said gas within said enclosed space. The flexible membrane is configured to reversibly flex into said enclosed space in response to pressure of a breast against the membrane. The flexure of the membrane causes a change in the pressure and volume of the gas within said enclosed space.

In some embodiments, the device can further include an analyzer for receiving said measured pressure and determining, based on said measured pressure, said change in the volume of said enclosed space. In some embodiments, the analyzer can determine the change in the volume of the enclosed space based on pressure versus volume calibration data. In some embodiments, the analyzer can determine the change in the volume of the enclosed space based on a theoretical relationship between the volume and pressure of the enclosed space. The analyzer can correlate a change in the volume of the enclosed space to the volume of the breast under examination based on calibration data.

In some embodiments, the analyzer can include an ASIC (Application Specific Integrated Circuit) that is programmed to calculate a change in the volume of said enclosed space in response to a measured change in pressure of the gas within said enclosed space due to flexure of said membrane.

The analyzer can be implemented in a variety of different ways. By way of example, in some embodiments, the analyzer can be implemented on a mobile device.

In some embodiments, the housing of the device can be bowl-shaped. The housing can be formed of a variety of different materials. In many embodiments, the permeability of the gas contained within the sealed enclosure through the material forming the housing is sufficiently low such that the device can be stored prior to use for at least about one year. A variety of materials can be employed for fabricating the housing. Some examples of suitable materials include, without limitation, PDMS (polydimethylsiloxane), polypropylene and/or polyethylene.

A variety of gases can be employed. Some examples of suitable gases include, air, nitrogen, and noble gases, such as helium.

The flexible membrane can also be fabricated using a variety of different polymeric materials, such as polyurethane.

In some embodiments, a device according to the present teachings can be used to determine whether the left and right breasts of a patient are substantially symmetric. For example, a difference between the pressure readings obtained by the device for the right and the left breasts can provide an indication of asymmetry (i.e., a difference in the volumetric sizes) of the two breasts. Such information can be useful, for example, for breast augmentation to ensure that appropriate implants are employed to obtain symmetry between the augmented breasts.

In another aspect, a device of measuring breast volume is disclosed, which comprises a housing providing an enclosure having an opening, and a flexible membrane that is coupled to the enclosure so as to provide a sealed chamber between the flexible membrane and an inner surface of the enclosure. A gas is disposed in the sealed chamber. At least one pressure sensor is coupled to the housing and is configured for measuring a pressure within the sealed chamber. The flexible membrane is configured to reversibly flex into said enclosed space in response to pressure of a breast against the membrane as the breast is received into said enclosure via said opening of the enclosure. The flexure of the membrane causes a change in the pressure and volume of said gas within said enclosed space. The pressure sensor can measure the change in the pressure and transmit the pressure data to an analyzer. The analyzer can receive the measured pressure and can determine, based on the measured pressure, the volume of the breast received within the enclosure.

By way of example, the analyzer can employ calibration data corresponding to pressure versus breast volume to determine the volume of the breast received within the enclosure. In some embodiments, such calibration data can be obtained by inserting a plurality of standardized volumes into the enclosure and measuring a change in the pressure within the sealed chamber observed in response to the receipt of the standardized volume within the enclosure. For example, 5-10 standardized volumes of different sizes can be employed to establish a calibration curve, which can be subsequently employed to correlate a measured change in the pressure of the sealed chamber with the breast volume.

The analyzer can be implemented in hardware, firmware and/or software using known techniques informed by the present teachings. By way of example, in some embodiments, the analyzer can include an ASIC (application specific integrated circuit) programmed to calculate a breast volume based on a pressure measured by the pressure sensor in response to insertion of the breast within the enclosure, which causes a flexure of the flexible membrane. In some embodiments, the analyzer can be implemented on a mobile device, such as a mobile phone, tablet, etc. In other embodiments, the analyzer can be implemented on a remote platform and can communicate with the pressure sensor via a network, e.g., the Internet.

In some embodiments, the housing is bowl-shaped with the enclosure having a substantially hemispherical profile, though other shapes can also be used. In general, the shape of the enclosure is selected to facilitate the insertion of a breast into the enclosure for measuring a volume thereof based on the present teachings. Similar to the previous embodiments, the sealed chamber can contain a variety of different gases. While in some embodiments, substantially a single gas type is used, in other embodiments, a mixture of two or more gases can be employed. Some examples of suitable gases include, without limitation, air, nitrogen and/or noble gases, such as helium. The housing and the flexible membrane can be formed of a variety of polymeric materials, such as those listed herein. In some embodiments, the flexible membrane has a thickness in a range of about 1 mm to about 5 mm, though other thicknesses can also be used so long as the flexure of the membrane in response to pressure exerted by the breast is sufficient to allow accurate measurement of the breast volume.

In another aspect, a breast-measuring device according to the present teachings can include two sensing units, each of which is configured to measure the volume of breast in a manner discussed herein. The two sensing units are coupled in a manner similar to how the two cups of a bra are coupled to one another so as to provide a bra-like device that can be worn by an individual. Each sensing unit can be implemented in a manner discussed above in connection with the previous embodiments to measure the volume of a breast. The device can be worn by an individual to obtain a measure of the volume of the individual's breasts. Such a device can be used, for example, by an individual at home, or can be employed by businesses that sell bras to ensure that a customer will receive a bra having the right size.

In another aspect, a system for measuring breast asymmetry is disclosed, which comprises a housing comprising an enclosure having an opening, a flexible membrane sealingly covering said opening so as to provide an enclosed space within said housing, a gas disposed within said enclosed space, and at least two pressure sensors coupled to said enclosure so as to measure pressure of said gas within said enclosed space. The flexible membrane is configured to reversibly flex into said enclosed space in response to pressure of a breast against the membrane. The flexure of the membrane causes a change in the pressure and volume of said gas within said enclosed space. An analyzer can receive the pressure readings of the two pressure sensors and obtain a measure of breast asymmetry based on a difference between those pressure readings.

In another aspect, a system for measuring breast asymmetry is disclosed, which comprises a device that includes a housing comprising an enclosure having an opening for receiving a breast, at least two gas-filled chambers fluidically isolated from one another, each of said chambers being formed between an inner wall of said enclosure and a flexible membrane, and at least two pressure sensors each of which is coupled to one of said gas-filled chambers for measuring gas pressure therein. Each flexible membrane is configured to reversibly flex in response to pressure of a breast thereon, thereby causing a pressure change in the respective chamber, where a pressure difference measured by said at least two pressure sensors is indicative of asymmetry of the breast. In some embodiments, a partition that is substantially impermeable to the gas contained in the chamber can separate the two chambers.

In some embodiments, the system can further include an analyzer for receiving the pressure readings from said sensors and utilizing said pressure readings to obtain a measure of asymmetry of the breast.

Further understanding of various aspects of the present invention can be obtained by reference to the following detailed description and the accompanying drawings, which are described briefly below.

DETAILED DESCRIPTION

The present teachings are generally directed to methods and systems for measuring the volumetric size and/or symmetry of an individual's breasts. In many embodiments, the device can include a gas-filled chamber having a flexible membrane, which can flex in response to a pressure exerted by a breast to cause a change in the pressure of the chamber. An analyzer can correlate the pressure change to a volume of the breast. Further, in some embodiments, the pressure readings obtained by using the device on the left and the right breast can be employed to determine a measure of asymmetry, if any, between the right and the left breast of an individual.

Various terms are used herein according to their ordinary meanings in the art. The term "about" as used herein is intended to indicate a variation of at most 10% around a numerical value. The term "substantially" as used herein is intended to indicate a variation of at most 10% relative to a complete state.

Figure 1:
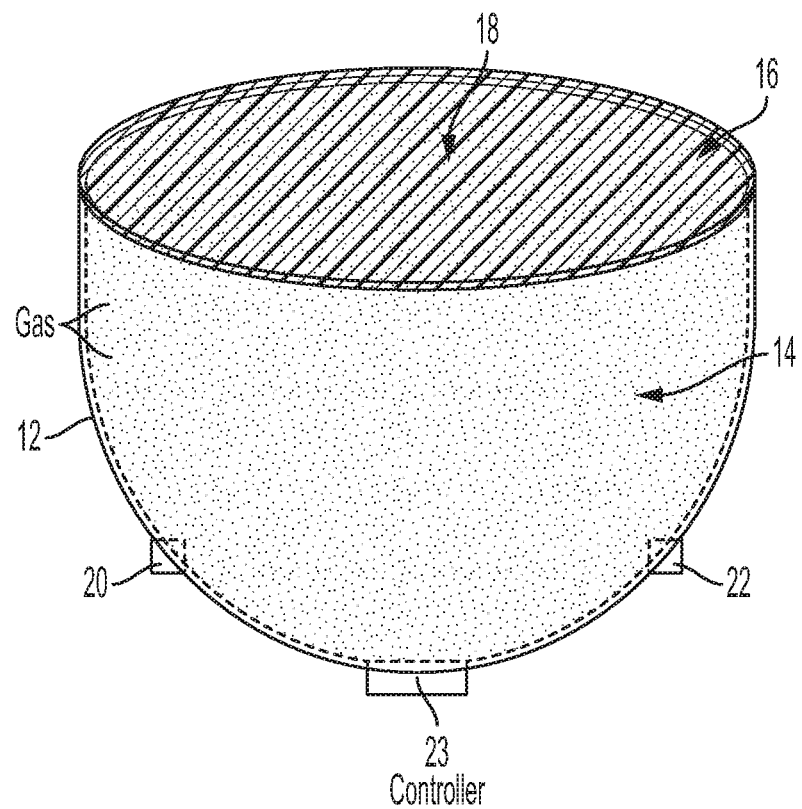
FIG. 1 schematically depicts a device according to an embodiment for measuring breast volume, FIG. 2 schematically depicts the device of claim 1, illustrating an analyzer that can receive pressure readings from the device to calculate a volumetric breast size, FIG. 3 schematically depicts an example of an implementation of an embodiment of analyzer suitable for use in a breast-measuring device according to the invention, FIG. 4 schematically depicts how a device according to the present teachings can be utilized to measure a breast size, FIG. 5 schematically depicts another embodiment of a device according to the present teachings for measuring the breast size, FIG. 6 schematically depicts the device of FIG. 5 in use for measuring an individual's breast size, FIG. 7A schematically depicts a front view of a bra-like device according to an embodiment having two breast-measuring units, FIG. 7B schematically depicts a rear view of the device of FIG. 7A, FIG. 8 schematically depicts an embodiment of a device according to the present teachings for measuring breast size, FIG. 9 schematically depicts an embodiment of a device according to the present teachings for measuring breast size, FIG. 10 schematically depicts an embodiment of a device according to the present teachings for measuring breast asymmetry, FIG. 11A schematically depicts an embodiment of a device according to the present teachings for measuring breast size, FIG. 11B schematically depicts the device of FIG. 11A receiving a breast, FIG. 12 schematically depicts an embodiment of a device according to the present teachings for measuring breast size, and FIG. 13 schematically depicts an embodiment of a device according to the present teachings for measuring breast size.
Figure 2:
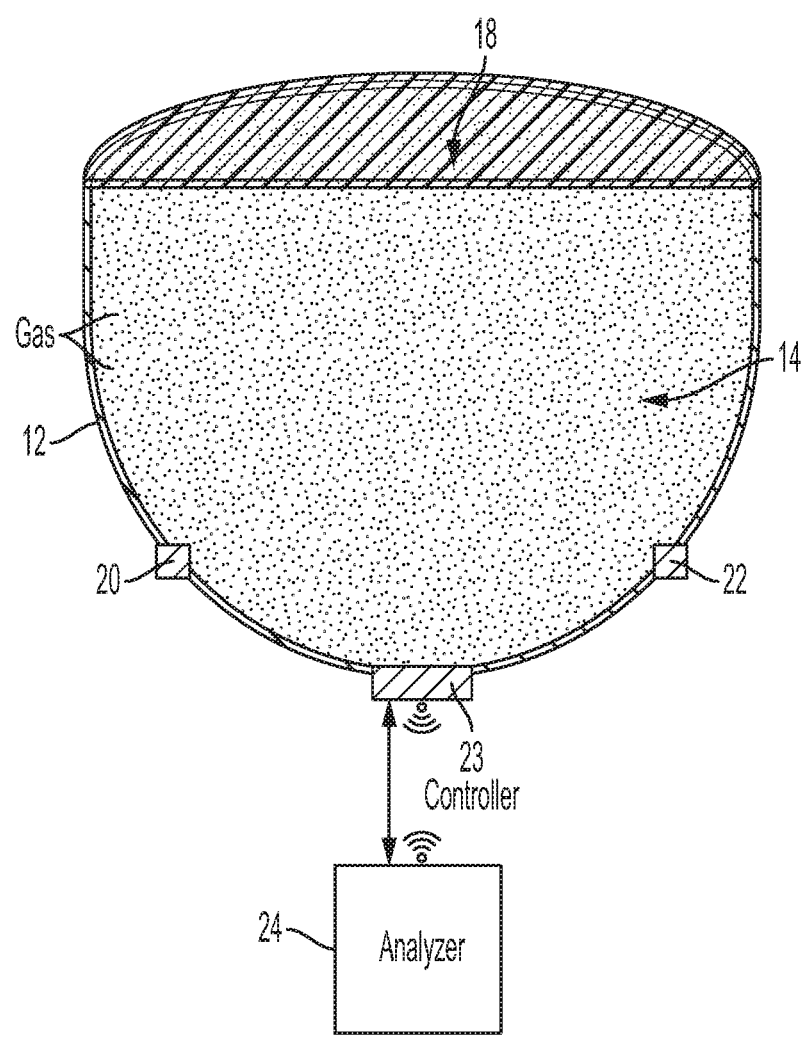
Figure 3:
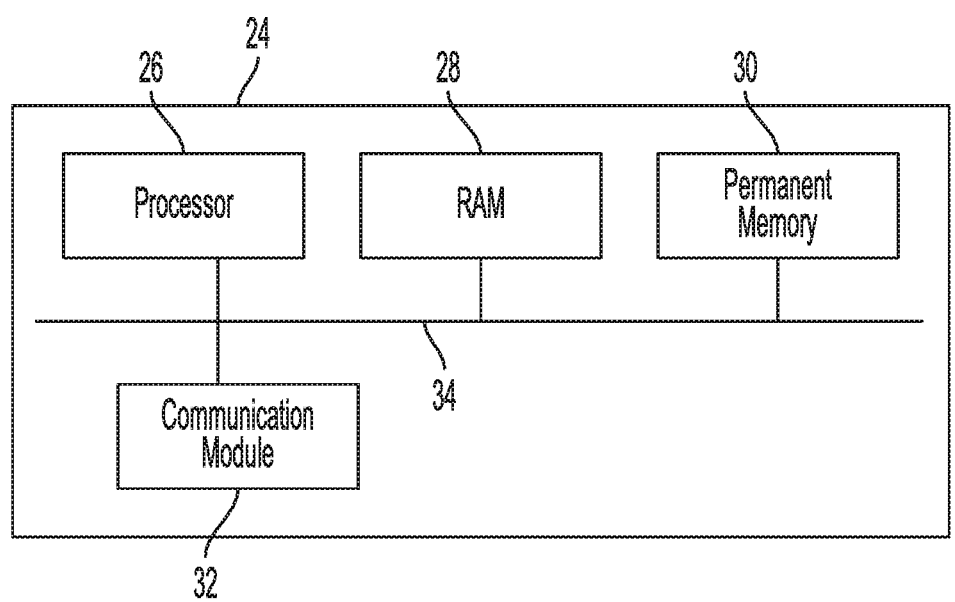

FIG. 1 schematically depicts a device 10 according to an embodiment for measuring breast volume size and symmetry, which includes a bowl-shaped housing 12 providing an enclosure 14 having an opening 16. A flexible membrane 18 covers the opening 16 so as to seal the enclosure and a gas contained therein from the external environment. The sealed enclosure 12 can contain a variety of different gases. For example, in some embodiments, the sealed enclosure can contain air while in other embodiments, the gas contained in the sealed enclosure can be primarily nitrogen. Further, in some embodiments, the sealed enclosure can contain a noble gas, such as helium.

In some embodiments, the gas contained in the sealed enclosure is at atmospheric pressure. In other embodiments, the gas contained in the sealed enclosure has a pressure greater than the atmospheric pressure. For example, the pressure of the gas contained in the enclosure can be in a range of about 1 atmosphere to about 5 atmospheres.

The flexible membrane is configured to reversibly flex in response to a pressure exerted by an individual's breast as the breast is pressed against the membrane. As the membrane flexes inward in response to the pressure exerted by the breast, the volume of the gas within the enclosure decreases in substantial proportion to the volume of the breast received within the flexed membrane. As discussed in more detail below, such a change in the volume of the gas contained within the sealed enclosure can be determined via measuring a change in the pressure of the gas contained within the sealed enclosure in response to the flexure of the membrane.

More specifically, with continued reference to FIG. 1, the device 10 further includes two pressure sensors 20 and 22 that are coupled to the housing 12 so as to measure the pressure of the gas contained within the sealed enclosure 12. As discussed below, a change in the pressure of the gas within the sealed enclosure measured by the pressure sensors 20 and 22 can be correlated to the volume of the breast received within the flexed membrane. The pressure sensors 20 and 22 can be coupled to the enclosure housing using a variety of different techniques. For example, they can be glued to an interior surface of the housing, or they can be placed within indentations provided on the interior surface of the housing. Although in this embodiment two pressure sensors are employed, in other embodiments, one pressure sensor or more than two pressure sensors can be used. A variety of different pressure sensors can be employed. Some examples of suitable pressure sensors include, without limitation, Model S pressure transducer marketed by Honeywell corporation, though a variety of other pressure transducers can also be employed.

In this embodiment, a controller 23 is coupled to the housing 12, for example, embedded within the wall thickness of the housing. The controller 23 can communicate with the pressure sensors to control their operation, as well as receive and communicate the measured pressures to an external analyzer 24.

The analyzer 24 can be configured, e.g., in a manner discussed below, to operate on the measured pressure to determine a change in the volume of the gas contained in the sealed enclosure. The identified change in the volume of the gas in the enclosure can then be correlated with the volume of the breast received within the flexed membrane. Further, in some embodiments, the analyzer can directly correlate the measured pressure to the breast volume based on previously-obtained calibration data.

Further, a difference between the pressure measured by pressure sensors 20 and 22 can be used to obtain a measure of asymmetry of the breast. For example, in some embodiments, asymmetric calibration implants can be employed to generate a calibration curve correlating a difference in the pressure readings of the sensors 20 and 22 with a measure of asymmetry of the breast.

The analyzer 24 can be implemented in hardware, firmware and/or software using known engineering techniques informed by the present teachings. By way of example, in this embodiment, the analyzer 24 includes a processor 26, a random memory module (RAM) 28, a permanent memory 30, a communication module 32 and a communication bus 34. The communication module 32 operating under the control of the processor 26 can communicate with the pressure sensors 20 and 22, via the controller 23, to receive values of the measured pressure. The processor can utilize the values of the measured pressure to calculate a change in the volume of the gas contained within the sealed enclosure. In some embodiments, the processor can employ an average of the pressure readings provided by pressure sensors 20 and 22.

For example, the processor can utilize a theoretical relationship correlating the pressure of the gas within the sealed enclosure to the gas volume to estimate the gas volume based on the measured gas pressure. One such theoretical relationship is as follows:

$$\Delta V = \frac{\kappa}{P_i^2} \Delta P \qquad \text{Eq. (1)}$$

where, $\Delta V$ signifies a change in the volume of the gas within the sealed enclosure in response to the pressure of a breast against the flexible membrane, $P_i$ signifies the initial pressure of the gas within the sealed enclosure (i.e., the gas pressure prior to the flexing of the membrane due to the pressure exerted by the individual's breast against the membrane);

$\Delta P$ denotes the change in the pressure of the gas within the sealed enclosure due to the flexure of the flexible membrane, and $\kappa$ is a constant that can be determined theoretically or via calibration of the device. For example, $\kappa$ can be determined theoretically as the product of the moles of gas contained in the sealed enclosure, the well-known gas constant (R), and temperature (T) in units of Kelvin.

Alternatively, $\kappa$ can be estimated by measuring a change in the pressure of the gas in the sealed enclosure in response to the flexure of the flexible membrane by using a plurality of standard volumes (e.g., standard implants).

In some embodiments, the gas pressure law that takes into account of the interactions between the molecules can be used. For example, the gas pressure relationship for diatomic gases can be employed when the enclosure is filled primarily with a diatomic gas, such as nitrogen.

In some embodiments, the device can be calibrated by using a series of standard implants having different volumes. For example, for each standard volume, the change in the pressure of the sealed gas can be measured when the standard volume is received in the flexed membrane. Such pressure measurements as a function of the standard volumes can then be employed to generate a calibration curve. The calibration curve can then be used to correlate a measured pressure change in response to the flexure of the membrane by a breast pressing against the membrane with the volume of the breast.

The analyzer 24 can be implemented in a variety of different ways. For example, in some embodiments, the analyzer can be implemented on a mobile device. In other embodiments, the analyzer can be implemented on a remote server that can communicate with the controller 23 and the associated pressure sensors via a network, e.g., the Internet.

Similar to the analyzer 24, the controller 23 can also be implemented in hardware, firmware and/or software using known techniques informed by the present teachings. Similar to the analyzer, the controller can include a processor, and associated memory for communicating and controlling the pressure sensors.

The housing can be formed from a variety of suitable materials. In many embodiments, the housing and the flexible membrane are formed of a material that can be sterilized, e.g., via autoclave, such that the device can be used in a surgical theater.

Figure 4:
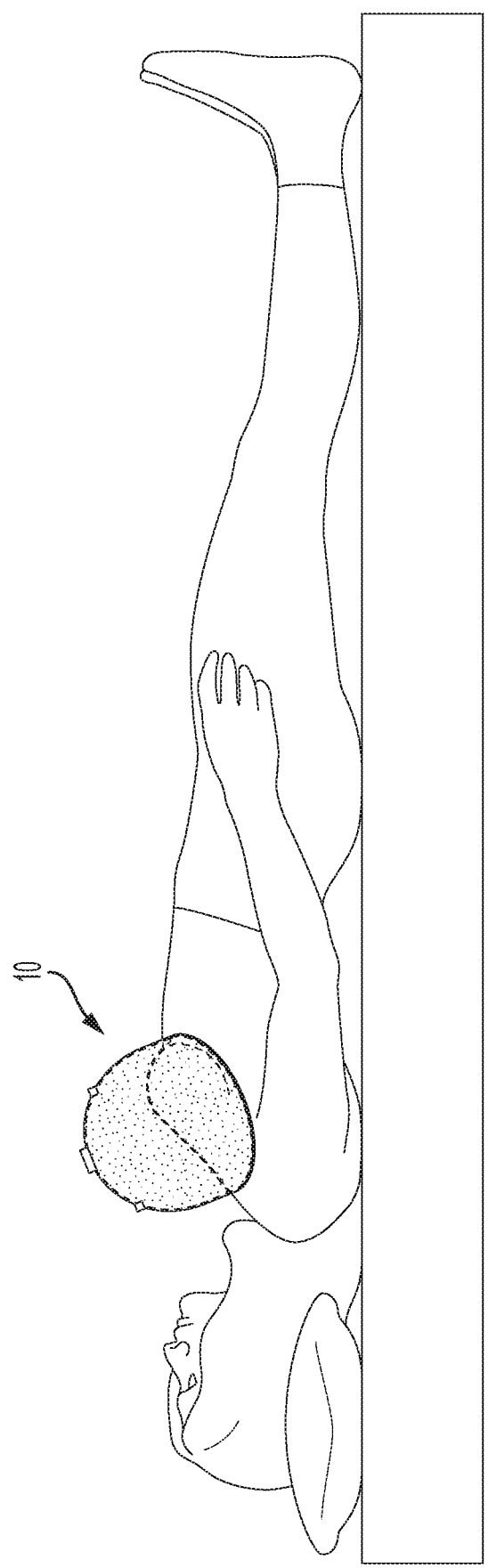

As shown in FIG. 4, in use, a device according to the present teachings, such as the above device 10, can be pressed against an individual breast so as to flex the membrane such that the membrane substantially collapses into the sealed enclosure, thus changing the pressure of the gas contained within the enclosure. Once the breast is fully received within the housing, the change in the pressure of the gas within the sealed enclosure is measured and analyzed to derive the volume of the breast. In some embodiment, a trigger button is provided to allow a user to indicate to the controller 23 that the analysis of the pressure data to determine breast volume should commence. Instead or in addition, the pressure differential between the pressure sensors 20 and 22 can be used by the analyzer to determine the degree of breast asymmetry. Although two sensors are employed in present embodiment, in other embodiments, more sensors, e.g., 3-20, sensors can be employed.

In some surgical procedures, such as breast augmentation, information about asymmetry between the right and the left breast of a patient, if any, is desired to ensure that the breasts are substantially symmetric after the surgery. In particular, in many such embodiments, information regarding an asymmetry between the left and the right breast (i.e., a difference between the volumetric sizes of the left and the right breasts) can be more important for the success of the surgical procedure than information regarding the absolute volume of the breasts. In such embodiments, a device according to the present teachings can be placed on each breast and pressure readings from one or more pressure sensors can be obtained. A difference between the pressure readings for the right and the left breasts, e.g., a difference between an average pressure reading from multiple sensors, can provide a measure of asymmetry between the two breasts within a desired tolerance. For example, in some embodiments, if a difference between the average pressure readings for the left and the right breasts is greater than about 10%, the left and the right breasts can be considered as asymmetric. This allows a surgeon to adjust the sizes of the two breasts such that the final breast sizes are substantially symmetric.

Figure 5:
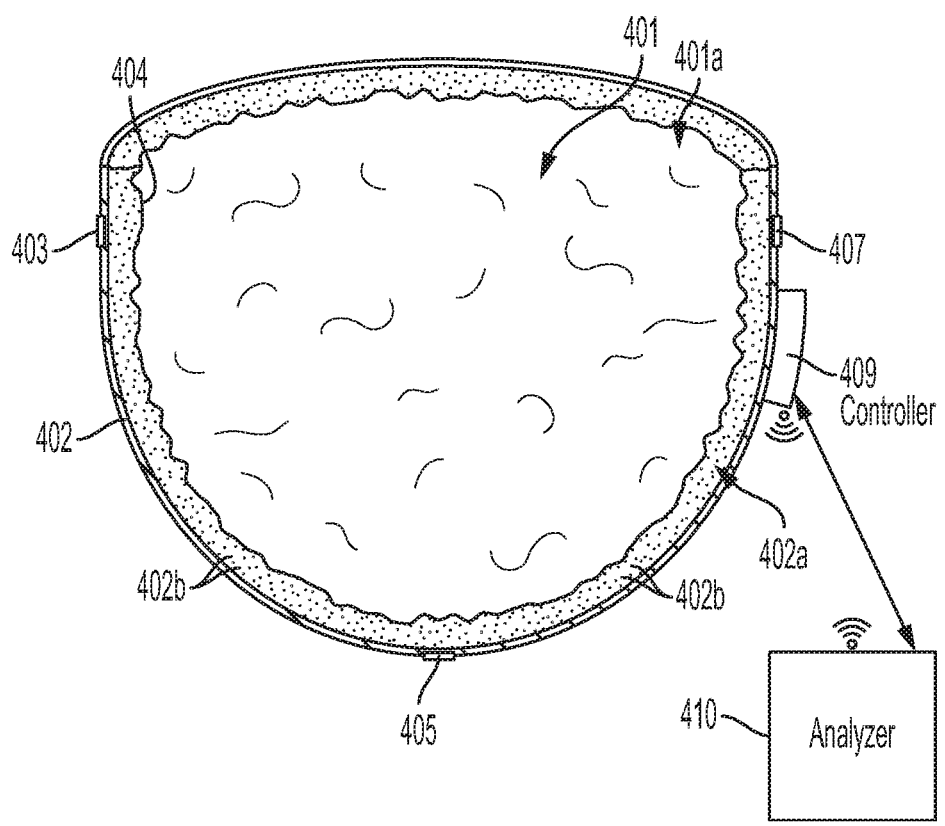

FIG. 5 schematically depicts a top view of another embodiment of a device 400 according to the present teachings for measuring volumetric breast size, which includes a bowl-shaped housing 402 for receiving a breast. A flexible membrane 404 is coupled to the inner surface of the bowl-shaped housing such that a sealed gas-filled (e.g., an air-filled) chamber 402a is formed between the flexible membrane and the inner surface of the bowl-shaped housing without fully covering the opening of the bowl-shaped housing. The sealed chamber 402a can contain one or more gases 402b. In this manner, a cavity 401 is provided for receiving a breast via the opening 401a. As the breast is received within the cavity 401, it presses against the flexible membrane 404 and hence causes a change in the volume of the gas-filled chamber, which can then be correlated to the breast size, as discussed in more detail below.

In some embodiments, the sealed chamber 402a contains a single gas type while in other embodiments, it can contain multiple gas types. Some examples of suitable gases include, without limitation, nitrogen, air, or a noble gas, such as helium.

In this embodiment, three pressure sensors 403, 405, and 407 are coupled to the housing so as to measure the pressure within the sealed chamber. Further, a controller 409 is coupled to the housing (e.g., it is coupled in this embodiment to an outer surface of the housing) for controlling the operation of the pressure sensors and to transmit pressure readings provided by the pressure sensors to an analyzer 410, which can use the pressure readings to arrive at the breast size and/or asymmetry, e.g., in a manner discussed above.

Similar to the previous embodiment, an analyzer 410 is in communication with the controller 409 to receive the pressure readings provided by the pressure sensors and to calculate the volumetric breast size and/or asymmetry based on those pressure readings.

Figure 6:
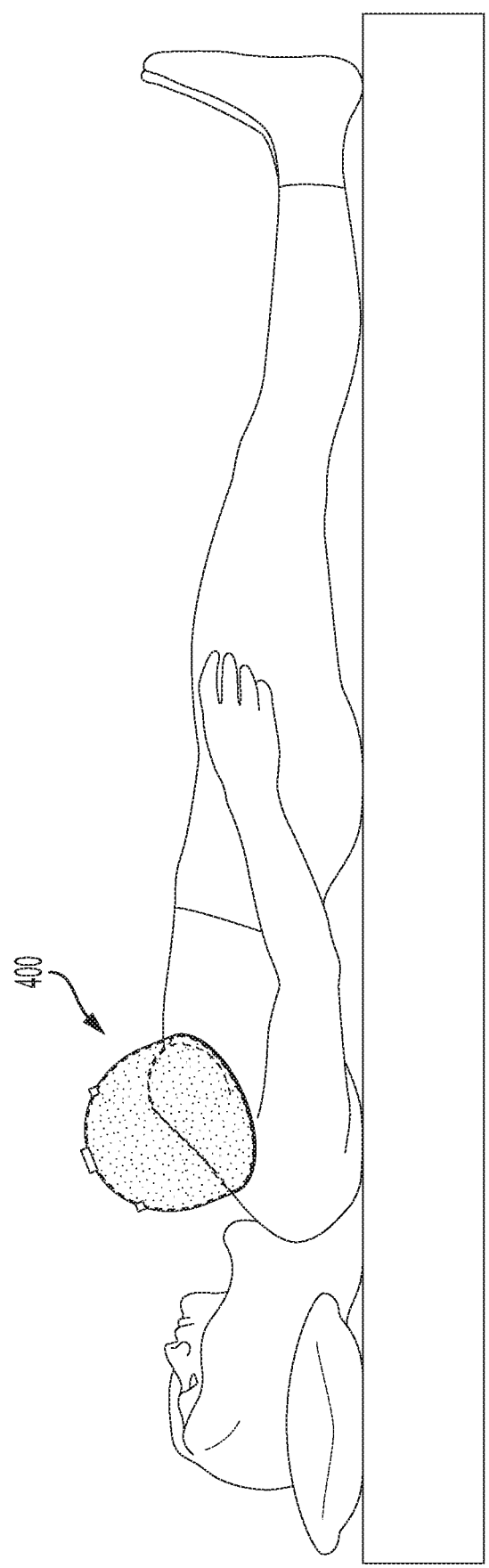

As shown schematically in FIG. 6, a breast can be received in the cavity provided by the bowl-shaped housing. As the breast is received within the cavity 401 provided in the bowl-shaped housing 402, the breast can press against the flexible membrane so as to cause flexure thereof and consequently a change in the volume of the sealed chamber. Once the breast is fully received in the housing 402, a change in the pressure of the sealed chamber in response to the flexure of the flexible membrane due to the pressure exerted thereon by the breast can be used to determine the volume of the breast in the following manner.

Specifically, the volume of the cavity 401 in absence of a breast within the cavity (and hence in the absence of the flexure of the flexible membrane 404) can be obtained theoretically and/or via calibration using a variety of different methods. By way of example, during the manufacturing of the device, after the sealed chamber is filled with an appropriate gas (e.g., air), the remaining volume within the cavity of the housing can be calibrated, e.g., using standard calibration volumetric elements.

To calculate the volume of the breast inserted into the cavity of the housing, the pressure readings provided by the pressure sensors 403/405/407 can be employed to determine a change in the volume of the sealed gas-filled chamber 402a, and this change can be added to the calibration volume of the remainder of the cavity to arrive at an estimate for the volume of the breast for which a volume measurement is desired. Further, a difference between the pressure readings of at least two of the sensors, or a composite of differences in pairwise pressure readings of the pressure sensors, can be employed to obtain a measure of the breast asymmetry.

The use of a device for measuring a breast volume according to the present teachings is not limited to an operating room. For example, a device according to the present teachings can be used during patient evaluation/education, prior to commencement of the surgical procedure, during or after the surgery. A device according to the present teachings can find other applications as well. For example, such a device can be employed to provide women an accurate measure of their breast size, e.g., for buying a bra.

Figure 7A:
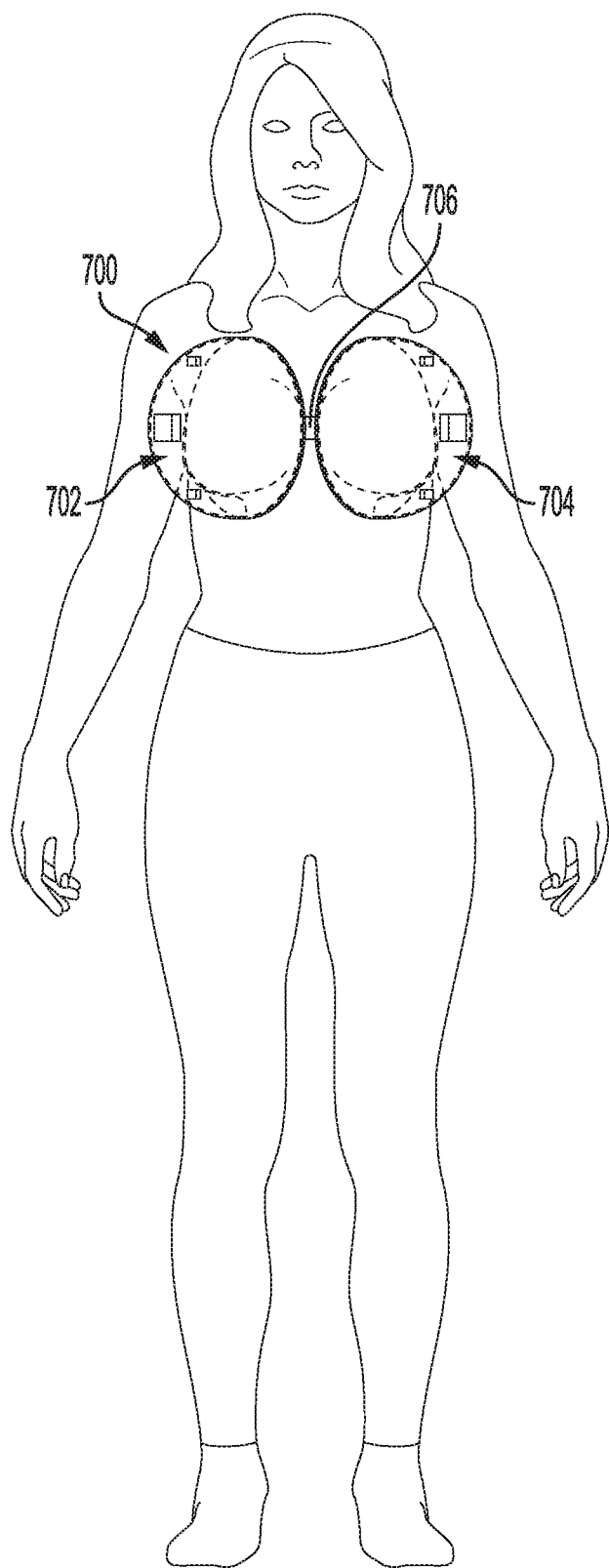
Figure 7B:
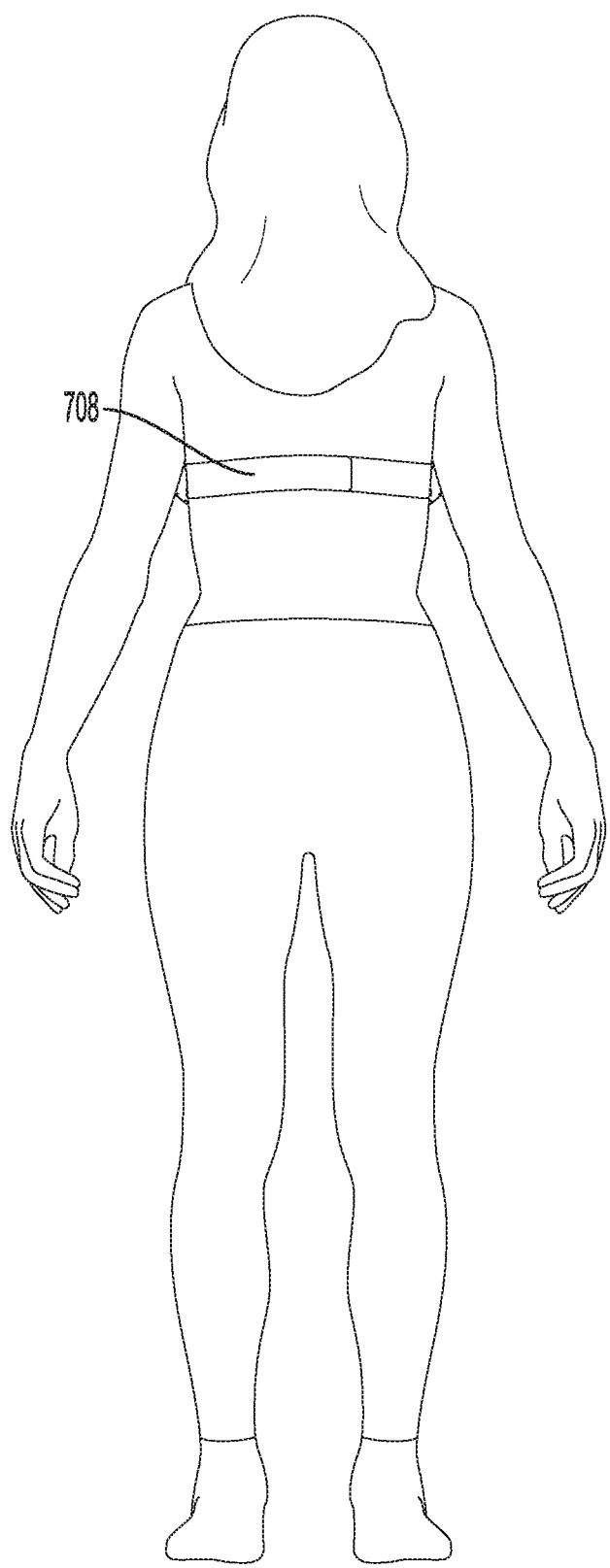

By way of example, FIGS. 7A and 7B schematically depict an implementation of a breast-measuring device 700 according to an embodiment, which can be worn by an individual for measuring her breast sizes. In this embodiment, the breast-measuring device 700 includes two breast-measuring units 702 and 704, each of which is configured in a manner discussed above to measure the size of a breast. The breast-measuring units 702 and 704 are mechanically coupled to one another by a natural and/or synthetic fabric 706, such as nylon or polyester. A strap 708 allows an individual to wear the device 700 similar to a bra with each of the breast-measuring units receiving one of the breasts.

With continued reference to FIG. 7, similar to the previous embodiments, a pressure change detected by each of the bra-measuring units can be received by an analyzer (not shown), e.g., an application executing on a mobile device (not shown). Similar to the analyzer discussed above, the application can employ the pressure readings to determine the volumetric size of each breast.

Figure 8:
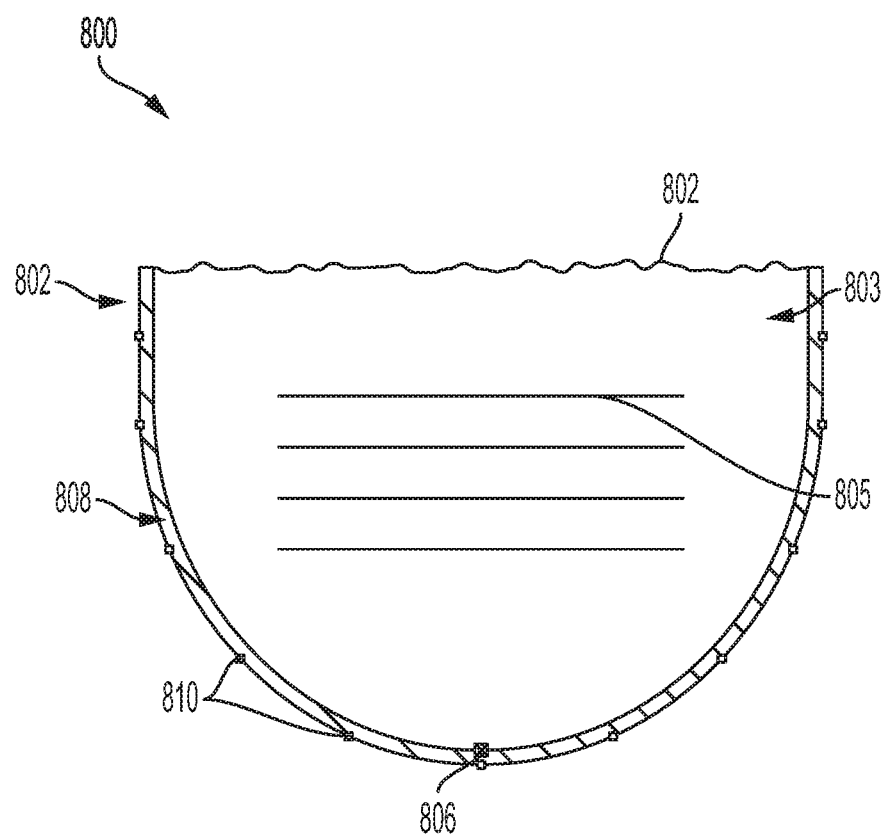

FIG. 8 depicts a device 800 according to another embodiment for measuring a volumetric breast size. The device 800 includes a bowl-shaped housing 802 providing a cavity 803, which is filled with a liquid 805, e.g., water or a mixture of water and alcohol. A flexible membrane 802 covers the top of the bowl-shaped housing. The cavity 803 is in fluid communication via a one-way valve 806 with an outer chamber 808. As a breast is pressed against the flexible membrane 802, the flexible membrane transmits the exerted pressure to the liquid 805, which in turn exerts a pressure on the one-way valve. As the breast continues to be received by the flexible membrane, the pressure on the one-way valve 806 increases until the valve opens and the outer chamber 808 begins to receive the fluid displaced due flexure of the flexible membrane 802. Once the breast is fully received into the housing via the flexure of the membrane 802, the volume of the liquid displaced from the cavity 803 into the outer chamber 808 can correspond to the volume of the breast.

In some embodiments, the wall of the outer chamber 808 is formed of a transparent material, e.g., transparent plastic, to allow visual inspection of the liquid received by the outer chamber. Further, calibrated graduated markings 810 can be provided on the outer chamber 808 to allow determining, via visual inspection, the volume of the liquid received by the outer chamber 808.

Similar to the previous embodiments, the inner wall of the cavity 803 can be formed of any suitable polymeric material, such as PDMS (polydimethylsiloxane), and the flexible membrane 802 can be formed of any suitable material, such a polyurethane. Further, the size of the device, including the diameter and depth of the cavity 803 can be in the ranges listed above, and can be adjusted based on the intended population of patients.

Figure 9:
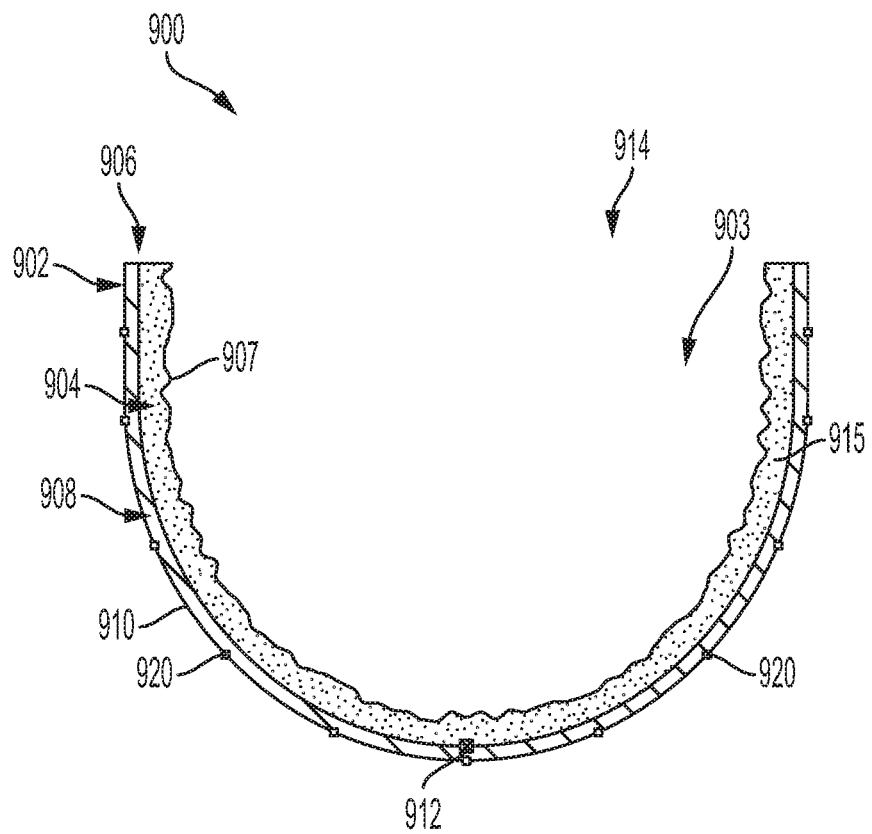

FIG. 9 schematically depicts a device 900 according to another embodiment, which includes a housing 902 providing a cavity 903. An inner liquid chamber 904 is formed between an inner wall 906 of the housing 902 and a flexible membrane 907. An outer chamber 908 is formed between the inner wall 906 and an outer wall 910. A one-way valve 912 fluidly connects the inner liquid chamber 904 to the outer chamber 908. The housing includes an opening 914 through which a breast can be received in the cavity 903. As the breast is received within the cavity 902, it presses against the flexible membrane 907 and hence exerts a pressure on a liquid 915 within the inner liquid chamber 904. Once the liquid pressure within the inner liquid chamber 904 reaches a threshold, the one-way valve opens and the liquid begins to enter the outer chamber 908. When the breast is fully received within the cavity 903, the volume of the liquid displaced from the inner chamber 904 to the outer chamber 908 can be determined, e.g., via visual inspection of a plurality of graduated markings 920 provided on the outer wall of the outer chamber.

Similar to the previous embodiment, the outer wall of the outer chamber can be formed of a transparent material, such as transparent plastic to facilitate visual inspection of the liquid displaced into the outer chamber.

Figure 10:
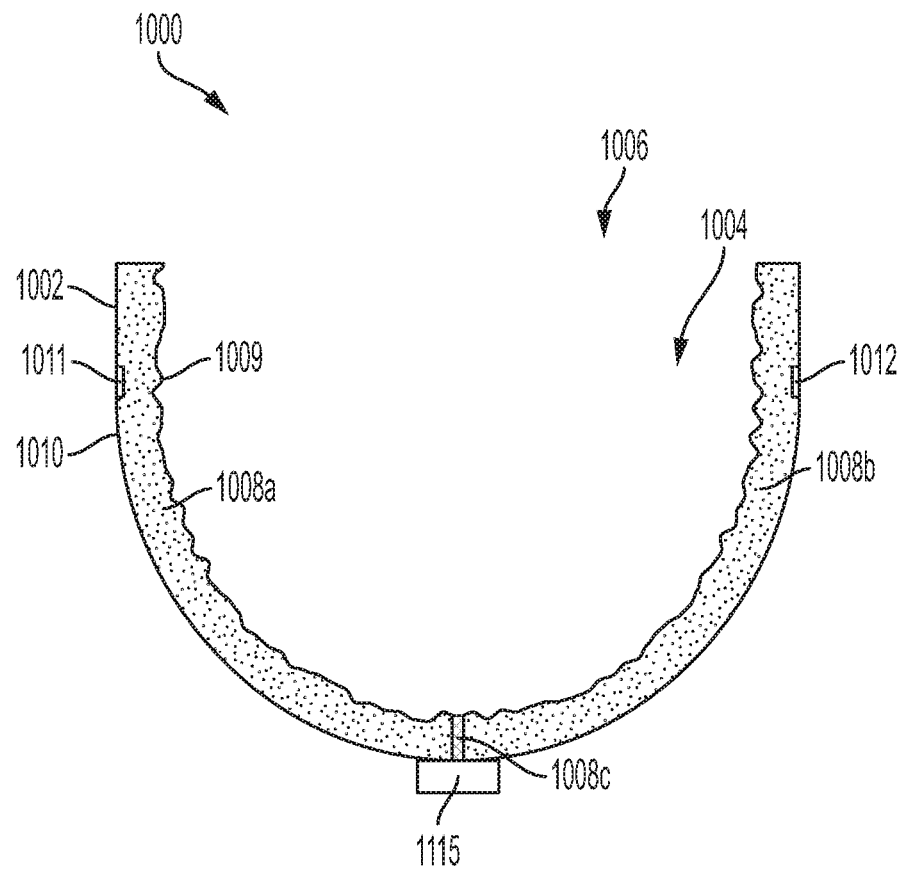

As discussed above, in some embodiments, a device according to the present teachings can be employed to obtain a measure of asymmetry of breasts. For example, in the above device 10, a difference in the pressure readings of the pressure sensors 20 and 22 can be employed to obtain a measure of the breast asymmetry. FIG. 10 shows another embodiment of a device 1000 according to the present teachings that can be employed for measuring breast asymmetry. The device 1000 includes a bowl-shaped housing 1002 providing a cavity 1004 having an opening 1006 through which a breast can be received within the cavity. Two gas-filled chamber 1008a and 1008b, separated by a substantially gas-impermeable partition 1008c is formed between a flexible membrane 1009 and an outer wall 1010 of the housing.

With continued reference to FIG. 10, a pressure sensor 1011 is coupled to the gas-filled chamber 1008a for measuring the pressure within that chamber, and a pressure sensor 1012 is coupled to the gas-filled chamber 1008b for measuring the pressure in that chamber. A controller 1115 controls the pressure sensors 1011 and 1012 and receives pressure data acquired thereby.

As a breast is received within the cavity 1004, it will exert a pressure on the flexible membrane 1009, thereby causing its inward flexure. The flexure of the membrane in turn increases the pressure in the chambers 1008a and 1008b. The increase in the pressure in the two chambers 1008a and 1008b can be different due to the right-left asymmetry of the breast. An analyzer (not shown), such as that discussed above in connection with the previous embodiments, can be used to receive the pressure readings and determine a measure of the breast asymmetry based on a difference between those readings, e.g., using calibration curves.

The devices according to the present teachings provide a number of advantages. For example, many insurance companies would pay for breast reduction surgery so long as the patient meets certain criteria. Since there is presently no objective way of measuring breast size, other measures (e.g., weight, height, symptoms) are employed to obtain rough estimates of the breast size. A device according to the present teachings can solve this problem by providing an objective measure of the volumetric size of the breast.

The sizes of various devices according to the present teachings can be selected to accommodate different breast sizes. For example, in some embodiments, the diameter of the above bowl-shaped housings can be, for example, in a range of about 2 inches to about 10 inches, e.g. in a range of 4 inches to 8 inches.

Figure 11A:
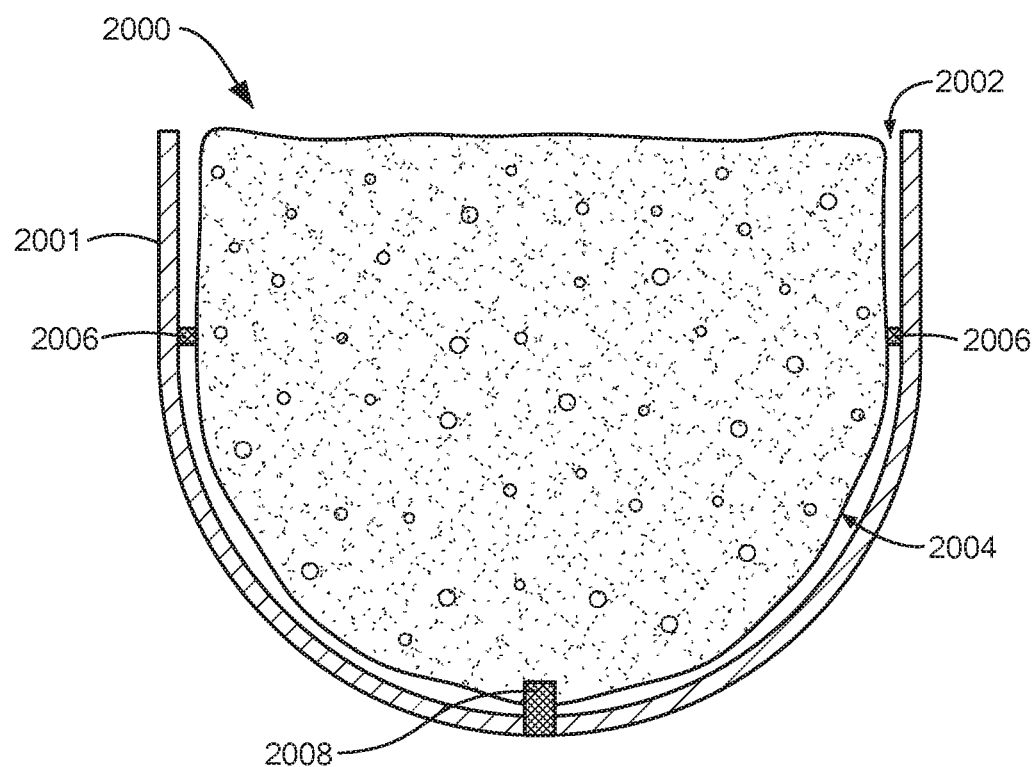

FIG. 11A schematically depicts another embodiment of a breast-measuring device 2000, which includes a housing 2001 providing a cavity 2002 in which a bladder 2004 is disposed. In the embodiment, the bladder is fixated to the housing 2001 via a plurality of attachment points 2006. In this embodiment, the bladder is filled with a gas, e.g., nitrogen. In some embodiments, the bladder can be filled with the gas up to a predefined pressure. Similar to the previous embodiments, a pressure sensor 2008 is operatively coupled to the bladder to measure the gas pressure within the bladder. The bladder is formed of a flexible material, e.g., polyurethane, which can flex in response to pressure of a breast thereon.

Figure 11B:
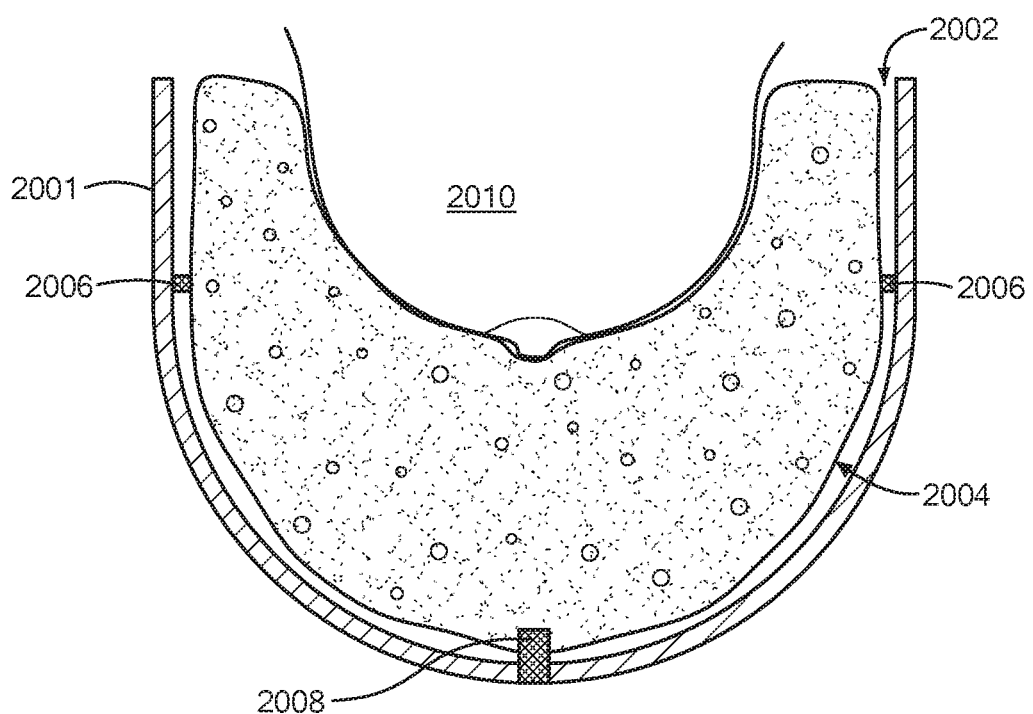

In use, the housing 2001 can be placed over a breast 2010 and the breast can be pressed against the exposed top portion of the bladder 2004. The pressure of the breast 2010 can flex the bladder's skin so as to provide a pouch for receiving the breast, as shown schematically in FIG. 11B. As the breast 2010 is pushed against the bladder and more of the breast is progressively received within the pouch generated in the bladder's skin, the increase in the pressure within the bladder can be monitored via the pressure sensor 2008. Once the breast 2010 is fully received within the pouch generated in the bladder 2004, the change in the pressure within the bladder, indicated by the pressure sensor 2008 can be utilized, e.g., in a manner discussed above, to obtain an estimate of the breast volume. In particular, similar to the previous embodiments, the change in the pressure within the bladder is related to the change in the volume of the bladder caused by the pressure exerted thereon by the breast. The change in the volume of the bladder is in turn related to the volume of the breast received within a pouch generated by the flexing of the bladder's skin (typically the change in the volume of the bladder is substantially equal to the volume of the breast received within a pouch generated within the bladder's skin due to the breast pressure). Hence, a change in the pressure within the bladder can be employed to provide an estimate of the volume of the breast.

Figure 12:
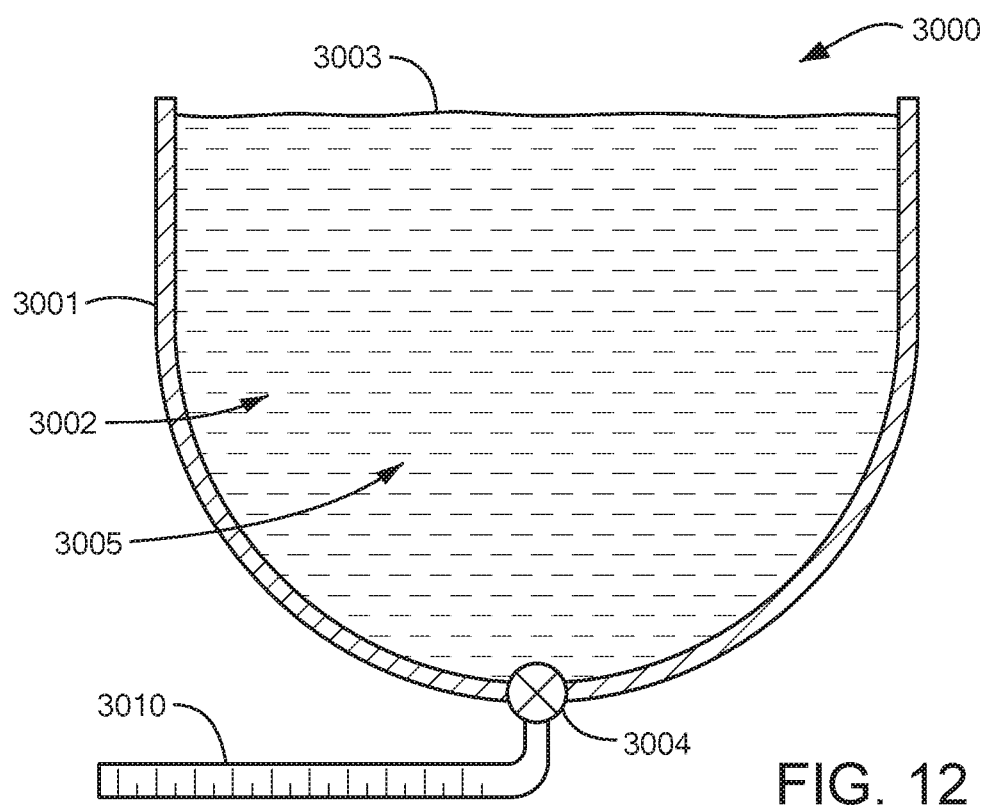

FIG. 12 schematically depicts another embodiment of a breast-measuring device 3000 according to another embodiment, which includes a housing 3001 providing a cavity 3002, which is sealed via a flexible membrane 3003. In this embodiment, the cavity 3002 is filled with an incompressible liquid 3005, e.g., water. A one-way valve 3004 couples the fluid-filled cavity to a visual indicator, e.g., a graduated cylinder 3010 in this embodiment, which is positioned outside the housing and is coupled thereto.

In use, the pressure of a breast on the flexible membrane can apply pressure to the liquid within the cavity 3002 and hence force the liquid within the cavity to exit through the one-way valve 3004 and enter the graduated cylinder. As the liquid is incompressible, the volume of the liquid within the graduated cylinder is directly proportional to the volume of the breast received within the flexed membrane 3003. The flexible membrane can be formed of a variety of polymeric materials, such as those discussed above (e.g., polyurethane).

Figure 13:
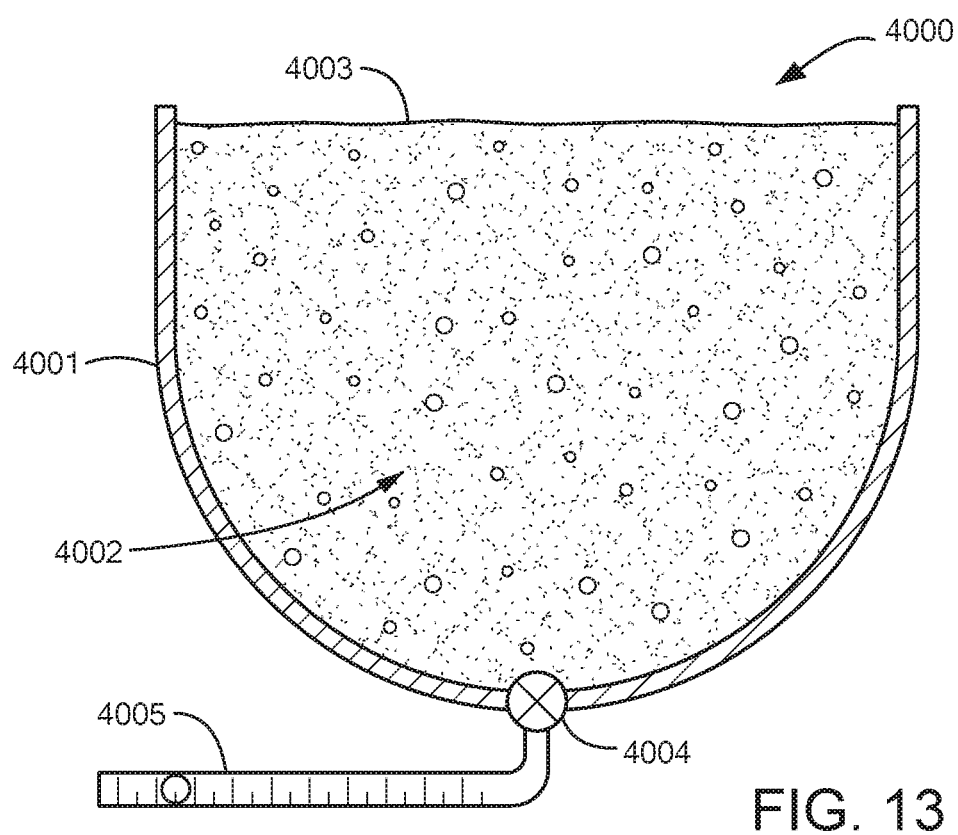

FIG. 13 schematically depicts another embodiment of a breast-measuring device 4000, which includes a housing 4001 providing a cavity 4002, which is sealed via a flexible membrane 4003. In this embodiment, the cavity is filled with a gas, e.g., nitrogen, and is in fluid communication via a one-way valve 4004 with a visual indicator 4005, e.g., a graduated cylinder in this embodiment.

In use, as a breast is pressed against the flexible membrane, the flexure of the membrane forces some of the gas within the cavity to exit through the one-way value into the graduated cylinder. As the volume of the gas forced into the graduated cylinder is proportional to the change in the volume of the cavity cause by the flexure of the membrane, the volume of the gas measured by the graduated cylinder can correspond to the volume of the breast received within the flexed membrane. In this embodiment, a ball 4005 within the graduated, calibrated cylinder allows facile determination of the volume of the gas exiting from the cavity through the one-way valve.

Those skilled in the art will appreciate that various changes can be made to the above embodiments without departing from the scope of the present invention.

What is claimed is:

1. A device for measuring breast volume, comprising:
a housing comprising an enclosure having an opening,
a flexible membrane sealingly covering said opening so as to provide an enclosed space within said housing,
a gas disposed within said enclosed space,
at least one pressure sensor coupled to said enclosure so as to measure pressure of said gas within said enclosed space,
wherein said flexible membrane is configured to reversibly flex into said enclosed space in response to pressure of a breast against the membrane; and
wherein said flexure of the membrane causes a change in the pressure and volume of said gas within said enclosed space,
an analyzer for receiving said measured pressure and determining, based on said measured pressure, said change in the volume of said enclosed space,
wherein said analyzer determines said change in the volume of the enclosed space based on pressure versus volume calibration data.

2. The device of claim 1, wherein said analyzer determines said change in the volume of the enclosed space based on a theoretical relationship between volume and pressure of said enclosed space.

3. The device of claim 1, wherein said analyzer comprises an ASIC (application specific integrated circuit) programmed to calculate a change in the volume of said enclosed space in response to a measured change in pressure within said enclosed space due to flexure of said membrane.

4. The device of claim 1, wherein said analyzer is implemented on a mobile device.

5. The device of claim 1, wherein said housing is bowl-shaped.

6. The device of claim 1, wherein said gas comprises a mixture of two or more gases.

7. The device of claim 1, wherein said gas comprises nitrogen.

8. The device of claim 1, wherein said gas comprises a noble gas.

9. The device of claim 1, wherein said gas comprises air.

10. The device of claim 1, wherein said housing comprises a polymeric material.

11. The device of claim 10, wherein said polymeric material comprise any of PDMS (polymethylsiloxane), polypropylene, and polyethylene.

12. The device of claim 1, wherein said flexible membrane comprises polyurethane.

13. The device of claim 1, wherein said flexible membrane has a thickness of in a range of about 1 mm to about 5 mm.

14. A system for measuring breast asymmetry, comprising:
  a housing comprising an enclosure having an opening,
  a flexible membrane sealingly covering said opening so as to provide an enclosed space within said housing,
  a gas disposed within said enclosed space,
  at least two pressure sensors coupled to said enclosure so as to measure pressure of said gas within said enclosed space,
  wherein said flexible membrane is configured to reversibly flex into said enclosed space in response to pressure of a breast against the membrane, and
  wherein said flexure of the membrane causes a change in the pressure and volume of said gas within said enclosed space,
  an analyzer for receiving pressure readings of said two pressure sensors and obtaining a measure of breast asymmetry based on a difference between said two pressure readings.

15. A system for measuring breast asymmetry, comprising:
  a device, comprising:
    a housing comprising an enclosure having an opening for receiving a breast,
    at least two gas-filled chambers fluidically isolated from one another, each of said chambers being formed between an inner wall of said enclosure and a flexible membrane,
    at least two pressure sensors each of which is coupled to one of said gas-filled chambers for measuring gas pressure therein,
    wherein each flexible membrane is configured to reversibly flex in response to pressure of a breast thereon, thereby causing a pressure change in the respective chamber,
    wherein a pressure difference measured by said at least two pressure sensors is indicative of asymmetry of the breast, and
  an analyzer configured to compute a measure of breast asymmetry based on said pressure change.

* * * * *